United States Patent [19]
Tur'yan et al.

[11] Patent Number: 5,635,043
[45] Date of Patent: Jun. 3, 1997

[54] DEVICE COMPRISING MICROCELL FOR BATCH INJECTION STRIPPING VOLTAMMETRIC ANALYSIS OF METAL TRACES

[76] Inventors: Yakov Tur'yan, 425 Neve Yaakov Street, Jerusalem 97350, Israel; Elena Strachkova, 8/19 Pineles Street, Jerusalem, Israel, 93283; Ilya Kuselman, 114/1 Neve Yaakov Street, Jerusalem 97390, Israel; Avinoam Shenhar, 31 Rav Usiel Street, Jerusalem, Israel

[21] Appl. No.: 573,391

[22] Filed: Dec. 15, 1995

[30] Foreign Application Priority Data

Dec. 19, 1994 [IL] Israel .................................. 112018

[51] Int. Cl.$^6$ .................................................. G01N 27/26
[52] U.S. Cl. ........................... 204/412; 204/413; 204/434; 205/775; 205/789.5
[58] Field of Search ............................ 204/400, 412, 204/413, 434; 205/775, 789.5

[56] References Cited

U.S. PATENT DOCUMENTS

| | | | |
|---|---|---|---|
| 3,329,599 | 7/1967 | Brewer | 204/413 |
| 3,421,989 | 1/1969 | Haagen-Smit | 204/413 |
| 3,859,193 | 1/1975 | Bednarski et al. | 204/412 |
| 4,302,314 | 11/1981 | Golimowski et al. | 204/434 |
| 4,725,339 | 2/1988 | Bindra et al. | 204/434 |

OTHER PUBLICATIONS

Ruedi Eggli, "Anodic Stripping Coulometry at a Thin-Film Mercury Electrode," *Analytica Chimica Acta*, 91 (1977) month unavailable 129–138.

Joseph Wang et al., "Batch injection stripping voltammetry of trace metals," *Analytica Chimica Acta*, 259 (1992) month unavailable 123–128.

*Primary Examiner*—T. Tung
*Attorney, Agent, or Firm*—Edwin D. Schindler

[57] ABSTRACT

A device for batch injection stripping voltammetric analysis of metal traces, of very high sensitivity. This sensitivity extends down to about 0.03 to 0.3 ppb for certain metals. The microanalysis can be carried out at a high rate and in addition to the high sensitivity is characterized by accuracy and high reproducibility. One of the main features is a novel microcell with a rotating working electrode of the mercury coated graphite type.

6 Claims, 3 Drawing Sheets

DEVICE COMPRISING MICROCELL FOR BATCH INJECTION STRIPPING VOLTAMMETRIC ANALYSIS OF METAL TRACES

FIELD OF THE INVENTION

The invention relates to the field of stripping voltammetric analysis of metal traces, including the design of an electrochemical micro-cell for micro-samples.

BACKGROUND OF THE INVENTION

Batch injection stripping voltammetry of trace metals has been used before for the analysis of trace metals in the ppb range. Amongst others there has been described a non-flow approach for anodic stripping voltammetry (ASV) of small discrete samples, using a batch injection operation. There has also been described anodic stripping coulometry at a thin-film mercury electrode where the charge contained in the stripping signal is used as indicator of traces of metals.

A variety of microcells has been described for voltammetry and for coulometric measurements.

The main requirements for a microcell for such analysis are, amongst others:

a. Provision for a microvolume sample;

b. Rotating electrode to decrease the detection limit; Batch injection of samples without interruption of the cathodic polarization of the working electrode, preventing mercury film oxidation on such electrode.

Microcells described in literature have certain drawbacks and are not entirely satisfactory.

The microcell-precursor (R. Eggli, Anal. Chim. Acta, 91 (1977) 129) consists of a microcompartment (100–600 mL) with a rotating working electrode, but this design does not allow the batch injection of samples. The use of such a microcell makes the analysis more complicated and time-consuming, and requires interruption of the working electrode cathodic polarization during replacement of a sample, which can cause oxidation of the mercury film on the working electrode. Using coulometric detection for anodic stripping voltammetry, the author has obtained a comparatively high detection limit. For lead it is 24–25 ppb at a deposition time equal to 12 min.

According to J. Wang et. al., Anal. Chim. Acta, 259 (1992) 123, a sample drop (100 mL) was put directly on a working electrode surface, which sample drop was surrounded by large volume of supporting electrolyte. The detection limit for anodic square-wave stripping voltammetry in this case was not too low due to the use of a static working electrode. For example, for lead the detection limit was equal to 1.2 ppb at a deposition time 0.5 min. At the same time batch injection of samples was used and the cathodic polarization of the working electrode was not interrupted. The sample throughput was 48 samples per hour. In spite of all precautions taken by the authors, the problem remained of how to avoid completely the mixing of a sample drop with the supporting electrolyte during the time when the drop was put into the cell and the deposition time.

SUMMARY OF THE INVENTION

A novel device for batch injection stripping voltammetric analysis of metal traces, comprising an improved microcell. A technique of analysis using such novel device and microcell.

There is provided a novel device for batch injection stripping voltammetry which comprises a novel design microcell, which overcomes shortcomings of existing cells for such types of analysis.

Thus, the invention comprises such a device incorporating such a microcell, and also a technique of analysis based on the use of such equipment.

The invention is illustrated hereinafter by way of example only, with reference to the enclosed schematical Figures, which are not according to scale and in which.

Figure 1:
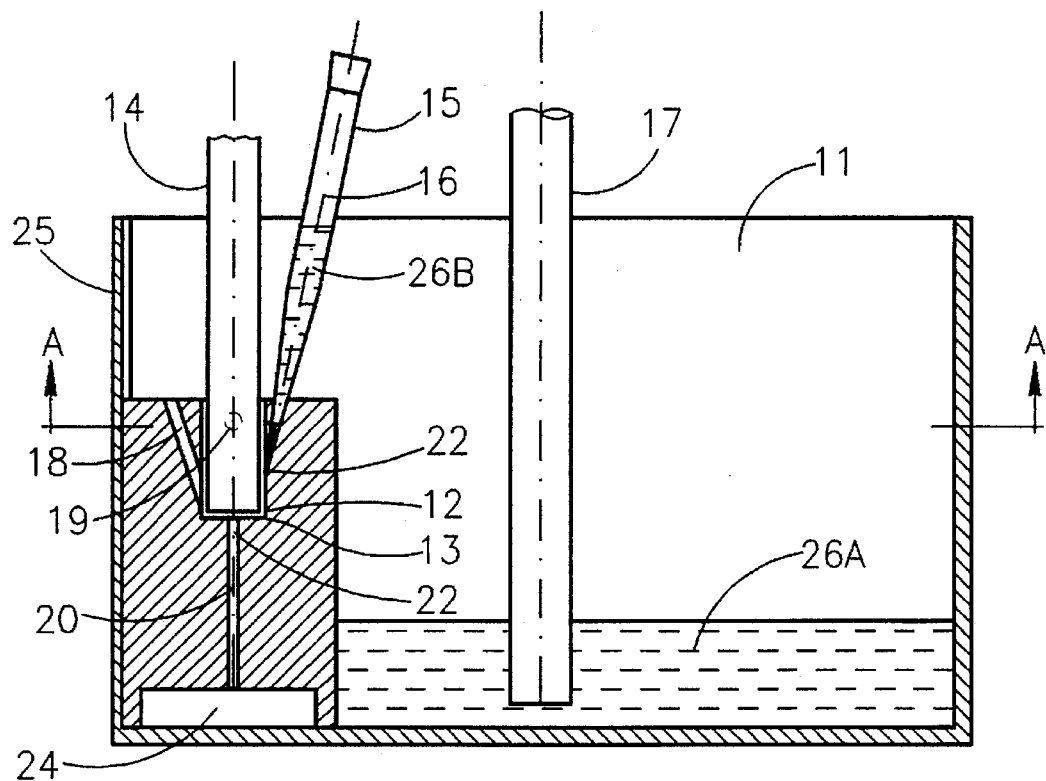
FIG. 1 is a sectional side view of a cell of the invention.
Figure 2:
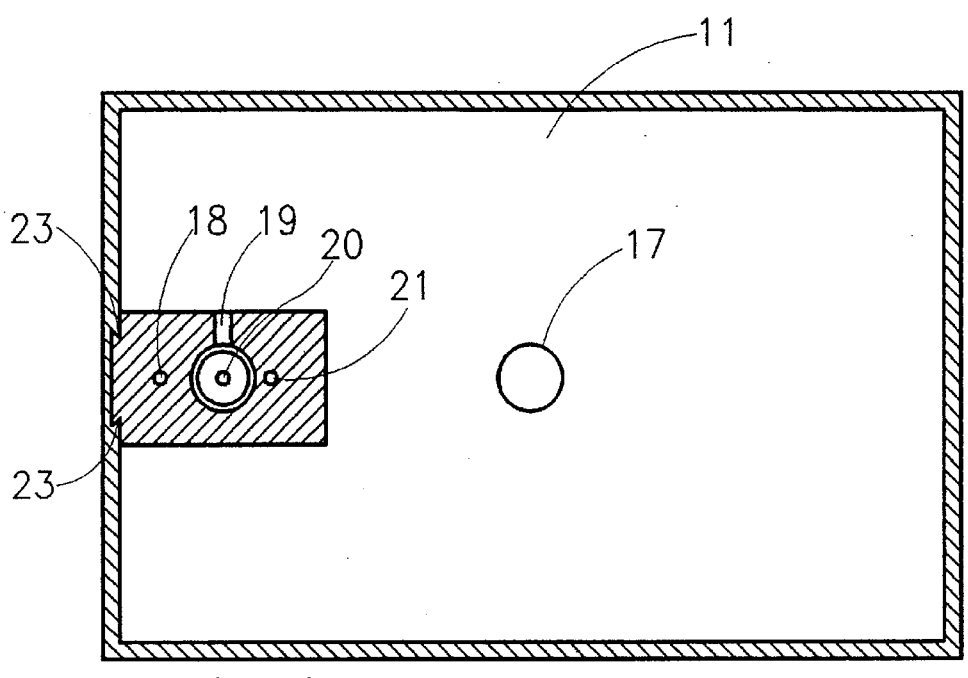
FIG. 2 is a sectional top view of the cell of FIG. 1.

As shown in FIG. 1, and FIG. 2, the device comprises in combination an outer large cell 11, wherein there is positioned inner microcell 12, into which there can be introduced sample 13, a rotating working electrode 14, a container 15 for an auxiliary electrode 16, a reference electrode 17 located in large cell 11, a channel 18 for sample injection, another channel 19 for sample removal, channels 20 and 21 for electrolytic contact with the reference and auxiliary electrodes 17 and 16, respectively, electrolyte plugs 22 and slots 23, and opening 24 and hole 25. In outer large cell 11 and container 15 there is provided, during analysis, an electrolyte 26a, 26b, respectively.

The device (FIG. 1 and 2) consists of inner microcell body 12 for the sample 13 and rotating working electrode 14, container 15 for auxiliary electrode 16 and electrolyte 26b, outer large cell 11 for reference electrode 17 and electrolyte 26a. The inner microcell 12 has four channels: channel 18 for batch injection of samples with the aid of an automatic pipette (for example, Gilson), channel 19 for removal of analyzed samples and washing solutions into outer large cell 11, channel 20 for electrolytic contact with the reference electrode, channel 21 for electrolytic contact with the auxiliary electrode and for fixing the auxiliary electrode container 15 (as the compartment a tip for Gilson pipette can be used). Channels 20 and 21 have electrolyte plugs 22 made of hardened ashless Whatman filter paper or of porous ceramics. Inner microcell 12 is removable due to special slots 23, which allows to work with different volumes of samples (200–600 mL) depending on channel 19 state and working electrode size. Container 15 intended for the auxiliary electrode also is removable which facilitates electrolyte replacement and plug 22 setting. Opening 24 in inner microcell 12 decreases the electric resistance; hole 25 is intended for a pipette installation into channel 18. Inner microcell 12 and outer large cell 11 are made of a transparent plastic such as "Plexiglas". The body of the outer large cell is fixed on a "Jack" platform with variable height, which facilitates setting the working electrode into the microcell.

THE TESTING TECHNIQUE FOR THE NOVEL MICROCELL

Anodic stripping voltammetric measurements were performed by means of "Polarecord" E-506 (Metrohm). The 1st harmonic a.c. voltammetric technique was used. The amplitude was 25 mV, the frequency –75 Hz, the scanning rate—40 mV/s. The rotating working electrode 6.1204.10 with graphite disk d 2 mm (Metrohm) and galvanic preplated mercury film was used. A Pt wire was used as an auxiliary electrode while the reference electrode was Ag/AgCl, KCl 0.1 mol/L.

The galvanic preplating of the mercury film on the working electrode was carried out daily in a separate cell with three electrodes (working, auxiliary and reference ones). Before galvanic preplating the graphite disk was treated with 3 mol/L $HNO_3$ and water, polished with aluminium oxide (BDH) 1.0 mm and 0.05 mm and again treated with water in an ultra-sound bath. The water used in the experiments was deionized and filtered through 0.2 mm Seralplus filter. The conditions of preplating of the mercury film were the following. The electrolyte $2.10^{-4}$ mol/L $Hg(NO_3)_2 + 2.10_{-3}$ mol/L $KNO_3 + 1.10^{-9}$ mol/L $Zn(NO_3)_2 + HNO_3$ (pH 4). The reagents were superpure ones from Merck. The electrolyte for preplating was deaerated by nitrogen. The potential for preplating was $-0.6$ V. The rate of the working electrode rotation was 500 rpm. The duration of preplating was 5 min. Ions of $Zn^{2+}$ were added to improve the adherence of the mercury film to the graphite surface.

After galvanic preplating and washing, the three electrodes were introduced into the device, filled by the supporting electrolyte.

The working electrode was kept at the potential of $-0.2$ V in intervals between stripping voltammetric analyses.

Lead ions were selected as model for testing the microcell. The determination of lead traces is very important (the problems of ecology and others); also this metal has been studied in detail under the conditions of stripping voltammetry.

The supporting electrolyte was 0.02 mol/L $KNO_3 + 1.10^{-3}$ M HCl. The initial Merck standard solution of lead (998±2 ppm) was diluted with the supporting electrolyte. The range of lead concentrations to be studied was 0.1–10 ppb. The solutions for stripping voltammetry were not deaerated which simplified and accelerated the analysis. The sample was introduced into inner microcell by Gilson pipette, 0.3 mL were used for washing and 0.3 mL—for the analysis. This operation was carried out at a rotation rate of the working electrode of 500 rpm. The duration of removing the previous sample and introduction of the new sample (600 mL) was 10 seconds.

The stripping voltammetric analysis was performed at a lead deposition time of 0.5 minute for concentrations 1–10 ppb, and a deposition time of 5.0 minutes for 0.1–1.0 ppb, at the potential of $-1.0$ V and rotation rate of the working electrode equal to 1000 rpm. Then the anodic stripping voltammetric a.c. wave was obtained, scanning a potential from $-1.0$ V to $-0.2$ V.

The duration of the scanning was 20 sec. The anodic peak of lead was reached at the potential of $-0.55$ V (Ag, AgCl, KCl 0.1 mol/L), which corresponds to the literature data. At the potential of $-0.2$ V the cleaning of the mercury film from lead was carried out during 0.5 min. Thus, the entire cycle of the stripping, voltammetric analysis at 0.5 min deposition time took 1.5 min, while at 5 min deposition time, the duration was 6 minutes.

The initial volume of the supporting electrolyte in the outer large cell 11 was 100 mL; due to the removal of the samples from inner microcell 12 this volume could be increased up to 200 mL. Thus, the number of determinations, taking into account washing of the inner microcell as well, may be 100 without removing the solution from the outer large cell.

THE RESULTS OF THE TEST

The test of the novel device comprising microcell has been carried out in accordance with the technique described above by means of anodic current peak (ip) measurements under the following conditions:

1) at a lead deposition time of 0.5 min for 0 (blank), 1,2,3,5 and 10 ppb in the supporting electrolyte Examples 1–6 in Table 1, respectively, 3 replicates for each for 5 mercury films;

2) at a lead deposition time of 5.0 min for 0 (blank), 0.1, 0.2, 0.3, 0.5 and 1.0 ppb in the supporting electrolyte Examples 7–12 in Table 2, respectively, each in 3 replicates for one (6-th) mercury film;

3) at a lead deposition time of 0.5 min for NIST Standard Reference Material SRM 1643c of Trace Elements in Water (certified lead concentration is 35.3±0.9 ppb) diluted 50 times with the supporting electrolyte and lead standard additions of 0, 1, 2, 4 ppb (examples 13–16 in Table 3, accordingly) each in 3 replicates for one (7-th) mercury film.

Based on these results, the following metrological characteristics of the analysis with the device, comprising novel microcell, were obtained.

TABLE 1

The results of the test of the novel microcell at lead deposition time 0.5 min

| Example Number | Pb conc., ppb | Replicate Number | Number of the film/Current ip, µA | | | | | $S_1$, % | $S_2$, % |
|---|---|---|---|---|---|---|---|---|---|
| | | | 1 | 2 | 3 | 4 | 5 | | |
| 1 | 0 | 1 | 0 | 0 | 0 | 0 | 0 | 0 | 0 |
| | | 2 | 0 | 0 | 0 | 0 | 0 | | |
| | | 3 | 0 | 0 | 0 | 0 | 0 | | |
| 2 | 1 | 1 | 0.021 | 0.021 | 0.021 | 0.021 | 0.021 | 0 | 0 |
| | | 2 | 0.021 | 0.021 | 0.021 | 0.021 | 0.021 | | |
| | | 3 | 0.021 | 0.021 | 0.021 | 0.021 | 0.021 | | |
| 3 | 2 | 1 | 0.036 | 0.036 | 0.036 | 0.036 | 0.039 | 2.38 | 3.71 |
| | | 2 | 0.036 | 0.033 | 0.036 | 0.036 | 0.036 | | |
| | | 3 | 0.033 | 0.033 | 0.036 | 0.036 | 0.039 | | |
| 4 | 3 | 1 | 0.054 | 0.054 | 0.057 | 0.06 | 0.057 | 1.49 | 3.29 |
| | | 2 | 0.054 | 0.054 | 0.054 | 0.057 | 0.06 | | |
| | | 3 | 0.054 | 0.054 | 0.054 | 0.057 | 0.057 | | |
| 5 | 5 | 1 | 0.09 | 0.087 | 0.093 | 0.096 | 0.09 | 1.76 | 2.75 |
| | | 2 | 0.09 | 0.09 | 0.093 | 0.096 | 0.093 | | |
| | | 3 | 0.087 | 0.09 | 0.096 | 0.093 | 0.096 | | |
| 6 | 10 | 1 | 0.168 | 0.171 | 0.186 | 0.189 | 0.189 | 1.06 | 4.66 |
| | | 2 | 0.168 | 0.168 | 0.189 | 0.183 | 0.183 | | |
| | | 3 | 0.171 | 0.168 | 0.186 | 0.186 | 0.183 | | |

TABLE 2

The results of the test of the novel microcell
at lead deposition time 5.0 min (film 6)

| Example Number | Pb conc., ppb | Replicate Number/Current i$_p$, μA | | |
|---|---|---|---|---|
| | | 1 | 2 | 3 |
| 7 | 0.0 | 0.012 | 0.012 | 0.012 |
| 8 | 0.1 | 0.027 | 0.027 | 0.027 |
| 9 | 0.2 | 0.042 | 0.039 | 0.042 |
| 10 | 0.3 | 0.054 | 0.057 | 0.057 |
| 11 | 0.5 | 0.090 | 0.090 | 0.087 |
| 12 | 1.0 | 0.168 | 0.171 | 0.168 |

TABLE 3

The results of the test of the novel microcell by the method
of standard additions (the analysis of SRM 1643c; film 7)

| Example Number | Pb addition, ppb | Replicate Number/Current i$_p$, μA | | |
|---|---|---|---|---|
| | | 1 | 2 | 3 |
| 13 | 0 | 0.018 | 0.018 | 0.018 |
| 14 | 1 | 0.039 | 0.039 | 0.039 |
| 15 | 2 | 0.063 | 0.063 | 0.066 |
| 16 | 4 | 0.111 | 0.114 | 0.111 |

Calibration Curve

Figure 3:
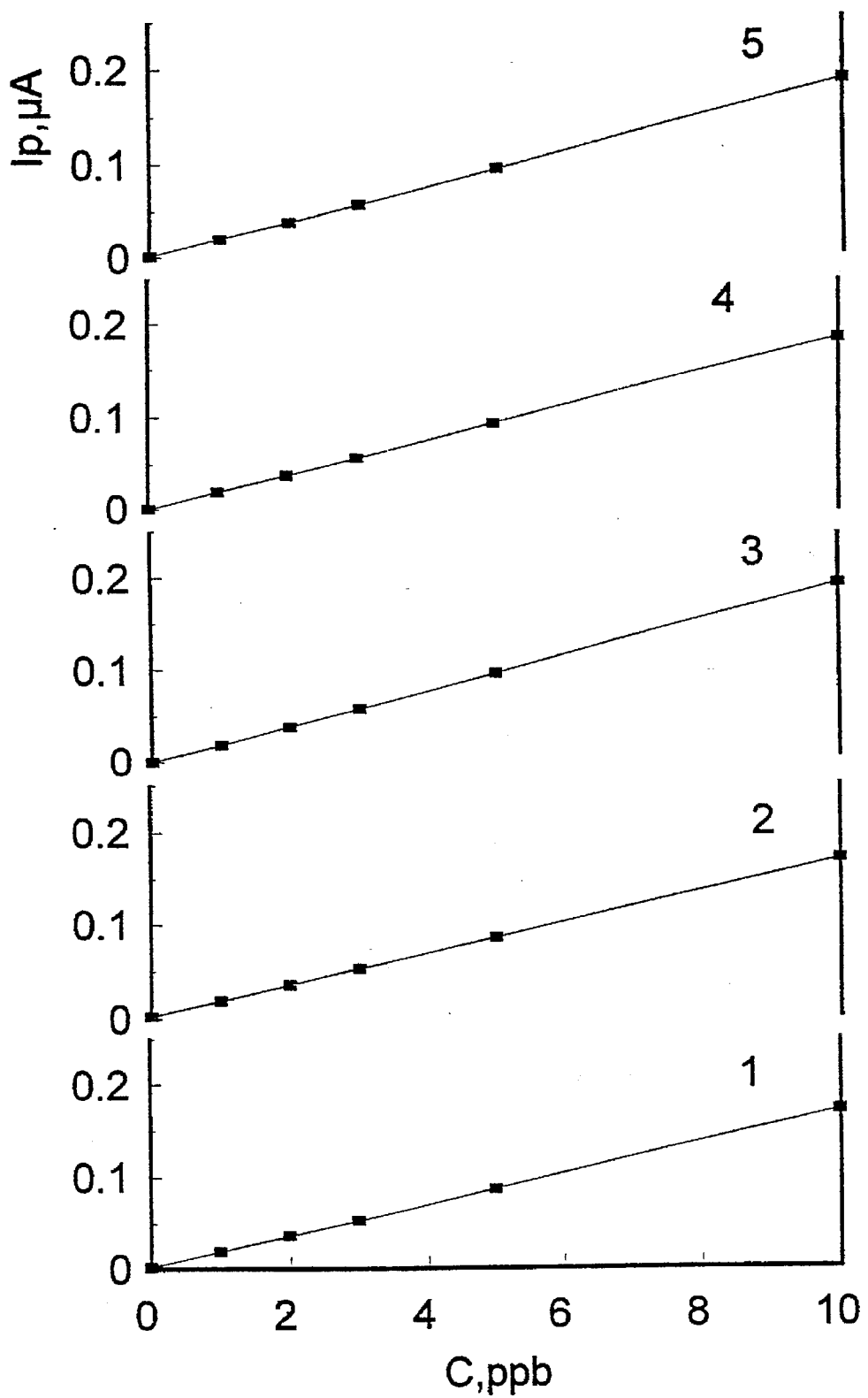
FIG. 3 is a presentation of calibration graphs of lead determination at deposition time 0.5 min.
Figure 4:
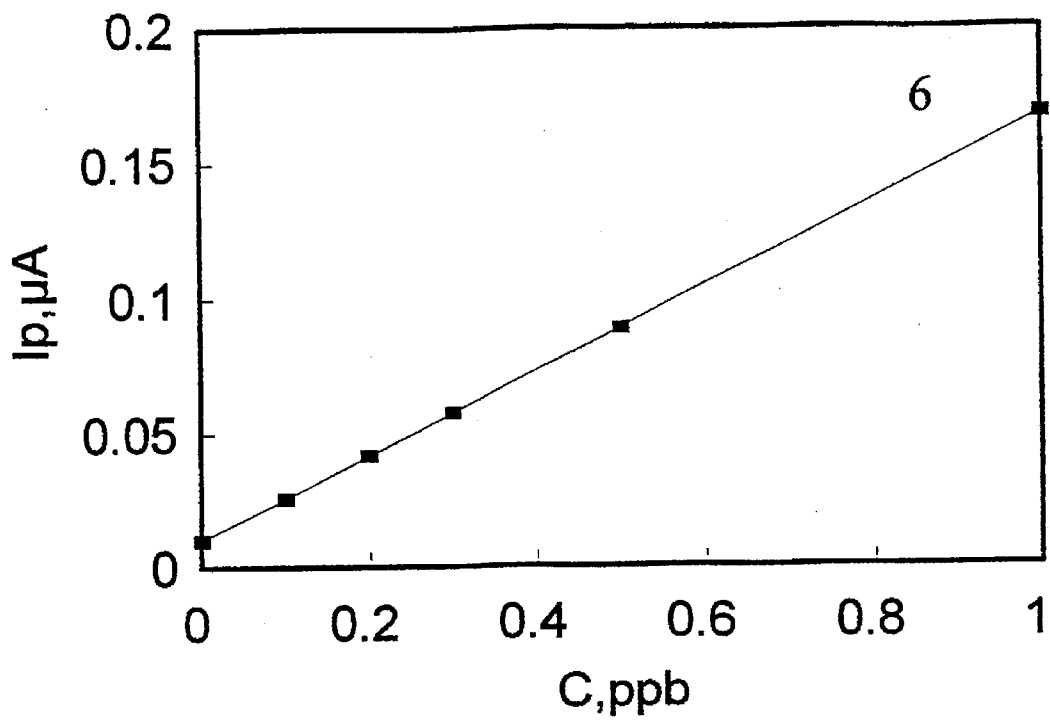
FIG. 4 is another calibration graph of lead determination at deposition time 5 min.
Figure 5:
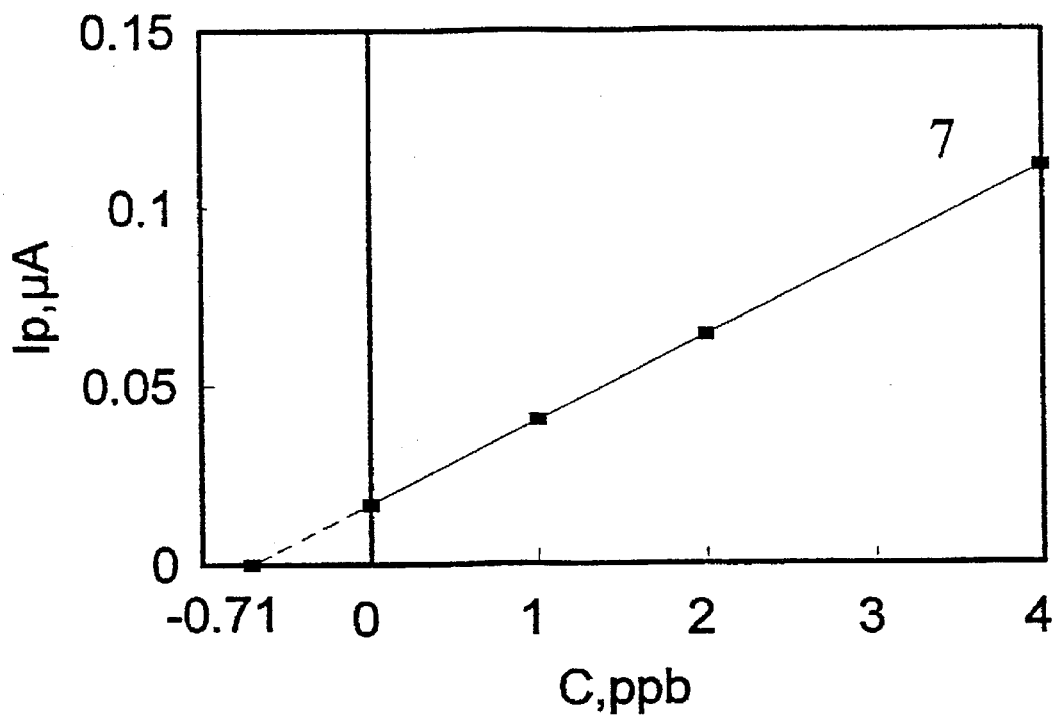
FIG. 5 is a calibration graph for lead determination in SRM 1643c at deposition time 0.5 min.

For each mercury film the calibration curves (current peak $i_p$ as function of the lead concentration C) were calculated on the basis of regression analysis and shown on FIG. 2–4. The numbers on the curves indicate the numbers of the mercury films. The curve on FIG. 4 differs from others because of the method of standard additions was used in this case. Linearity of the curves as correlation coefficient is shown in Table 4: all values of correlation coefficient are not less 0.998, i.e. sufficient.

TABLE 4

Correlation coefficient and detection limit

| Characteristic | Numbers of the mercury film | | | | | | |
|---|---|---|---|---|---|---|---|
| | 1 | 2 | 3 | 4 | 5 | 6 | 7 |
| Corr. coeff. | 0.999 | 0.998 | 0.999 | 0.999 | 0.999 | 0.999 | 0.998 |
| Det. limit, ppb | 0.33 | 0.35 | 0.22 | 0.27 | 0.27 | 0.03 | — |

Detection Limit

On the basis of the known technique (Grant T. Wernimont. Use of Statistics to Develop and Evaluate Analytical Methods, AOAC, USA, 3-nd ed., 1990) the detection limit has been calculated from calibration curves 1–6. The calculation was carried out for the probabilities of false lead detection and false non-detection (type I and type II errors) equal to 5%. Results of the calculations for different mercury films and different lead deposition times are shown in Table 4. The values for lead deposition time 0.5 min (curves 1–5, FIG. 2) are 4–5 times lower than the detection limit 1.2 ppb obtained by J. Wang et al., Anal. Chim. Acta, 259 (1992) 122. The value 0.03 ppb we obtained for lead deposition time 5.0 min (curve 6, FIG. 3) is about 10 times lower than that for lead deposition time 0.5 min. For comparison, in the microcell (K. Stulik and M. Stulikova, Anal Lett., 6(1973) 441) for lead deposition time 10 rain it the detection limit obtained was only 0.2 ppb.

Repeatability and Reproducibility

These characteristics were analyzed based on data in Table 1.

The repeatability was evaluated as an average relative standard deviation between the replicates at a given lead concentration:

$$S_1 = \left\{ \sum_{i=1}^{5} \left[ \sum_{j=1}^{3} (X_{ij} - \bar{X}_j)^2 / 2\bar{X}_i \right] / 5 \right\}^{0.5} 100\%,$$

where $X_{ij}$ is a result of j-th replicate measurement of current peak (j=1,2,3) for i-th mercury film (i=1,2, . . . , 5);

$$\bar{X}_i = \sum_{j=1}^{3} X_{ij}/3$$

The reproducibility was evaluated as the relative standard deviation between the results of average current peak measurements for each mercury film at a given lead concentration:

$$S_2 = \left\{ \left[ \sum_{i=1}^{5} (\bar{X}_i - \bar{\bar{X}})^2 / 4\bar{\bar{X}} \right] \right\}^{0.5} 100\%$$

where $$\bar{\bar{X}} = \sum_{i=1}^{5} x_i/5.$$

From Table 1 one can see that $S_1 < 2.5\%$ and $S_2 < 5\%$. It is sufficient even for stripping voltammetry with macrocells.

Accuracy

The accuracy was evaluated as the bias of the analytical result obtained by the standard additions method from the certified value for SRM 1643C (35.3±0.9 ppb). As can be seen in FIG. 4 the lead concentration in the microcell is 0.71 ppb. Due to the 50-time dilution we used, the result of our analysis for SRM 1643c is 0.71×50=35.5 ppb. Since the bias 35.5−35.3=0.2 ppb is less than the uncertainty of the certified value (±0.9 ppb), that the accuracy can be considered sufficient.

Rate of Analysis

The high rate of the analysis has been obtained. At deposition time equal to 0.5 min the sample throughput is 40 samples per hour. At deposition time equal to 5 min the sample throughput is 10 samples per hour.

Amongst the advantages of the novel analytical device are the microcell which combines sample batch injection with a rotating working electrode. This combination allows a very low detection limit, in the 0.03 ppb to 0.3 ppb range. This is lower than that for known microcells, at high analysis rates. The accuracy, reproducibility and repeatability of results thus attained are equal to those obtainable of stripping voltammetry using macrocells. The rate of sample analysis is comparatively rapid and thus the novel design makes possible accurate measurements at ultra-low concentrations at a high analysis rate.

We claim:

1. A device for use in batch injection stripping voltammetric analysis of metal traces comprising in combination an outer cell housing a reference electrode and an inner microcell, said inner microcell containing a rotating working electrode of graphite coated with a mercury layer, and said inner microcell being connected with a container housing an auxiliary electrode, a channel for sample introduction into the inner microcell and a channel for removing such sample after analysis and for flushing into the outer cell, channels for electrolyte contact between the rotating electrode and the auxiliary and reference electrodes, and porous electrolyte plugs between the inner microcell and the channels leading to the auxiliary and reference electrodes.

2. A device according to claim 1, where the inner microcell cell is removable from the outer cell.

3. A device according to claim 1, where the container housing the auxiliary electrode is removable from the inner microcell.

4. A device according to claim 1, where the rotating working electrode comprises a graphite disk.

5. A device according to claim 1, comprising means for maintaining the working electrode under cathodic polarization during the period of time of sample replacement.

6. A device according to claim 1, where the rotating working electrode comprises a graphite disk preplated with mercury from a solution of mercury nitrate, potassium nitrate and zinc nitrate, at a potential of about 0.6 V.

* * * * *